United States Patent [19]
Alt et al.

[11] Patent Number: 6,162,936
[45] Date of Patent: Dec. 19, 2000

[54] ORGANOMETALLIC FLUORENYL COMPOUNDS, PREPARATION, AND USE

[75] Inventors: Helmut G. Alt, Bayreuth, Germany; Syriac J. Palackal, Bartlesville, Okla.; Konstantinos Patsidis, Bayreuth, Germany; M. Bruce Welch, Bartlesville, Okla.; Rolf L. Geerts, Bartlesville, Okla.; Eric T. Hsieh, Bartlesville, Okla.; Max P. McDaniel, Bartlesville, Okla.; Gil R. Hawley, Dewey, Okla.; Paul D. Smith, Seabrook, Tex.

[73] Assignee: Phillips Petroleum Company, Bartlesville, Okla.

[21] Appl. No.: 09/085,945

[22] Filed: May 28, 1998

Related U.S. Application Data

[60] Continuation of application No. 08/352,936, Dec. 9, 1994, which is a division of application No. 07/734,853, Jul. 23, 1991, Pat. No. 5,436,305, which is a continuation-in-part of application No. 07/697,363, May 9, 1991, Pat. No. 5,191,132.

[51] Int. Cl.$^7$ .............................. C07F 9/00; C07F 17/00; C07F 7/00; C07F 7/28
[52] U.S. Cl. ................................ 556/43; 556/53; 556/56
[58] Field of Search .................... 556/11, 12, 43, 556/53, 56; 502/103, 117, 152

[56] References Cited

U.S. PATENT DOCUMENTS

| | | | |
|---|---|---|---|
| 4,015,059 | 3/1977 | Karol | 526/130 |
| 5,162,278 | 11/1992 | Razavi | 502/152 |
| 5,191,132 | 3/1993 | Patsidis et al. | 585/375 |
| 5,252,677 | 10/1993 | Tomita et al. | 526/160 |
| 5,304,523 | 4/1994 | Razavi | 502/152 |
| 5,436,305 | 7/1995 | Alt et al. | 526/160 |
| 5,589,556 | 12/1996 | Razavi | 526/170 |
| 5,610,247 | 3/1997 | Alt et al. | 502/152 |
| 5,627,247 | 5/1997 | Alt et al. | 502/152 |
| 5,780,659 | 7/1998 | Schmid et al. | 556/56 |

FOREIGN PATENT DOCUMENTS

| | | |
|---|---|---|
| 64-66214 | 3/1989 | Japan . |
| 2/173111 | 7/1990 | Japan . |
| 2/173112 | 7/1990 | Japan . |
| 934281 | 8/1963 | United Kingdom . |

OTHER PUBLICATIONS

Chem. Abstracts, vol. 75, p. 73, abstract 7386n., 1971.
"Electronic and Steric Influence of the Cyclopentadienyl Substituents and the Role of the Bridge on the Catalytic Behaviour of Ansa Metallocene Complexes in Stereospecific Polymerization of alpha–Olefin in Homogeneous Catalysis", A. Razavi, SPO Paper, pp. 167, 172, 177, 1992.
E. Samuel et al., J. Organomet. Chem., vol. 113, pp. 331–339., 1976.
E. Samuel et al., J. Organomet. Chem., vol. 4, pp. 156–158., 1965.

*Primary Examiner*—Mark L. Bell
*Assistant Examiner*—J. Pasterczyk
*Attorney, Agent, or Firm*—Edward L. Bowman

[57] ABSTRACT

Fluorenyl-containing metallocenes are disclosed along with methods for making the metallocenes. Also disclosed are methods for using the metallocenes as polymerization catalysts. In addition, polymers resulting from such polymerizations are disclosed.

5 Claims, No Drawings

ORGANOMETALLIC FLUORENYL COMPOUNDS, PREPARATION, AND USE

This application is a continuation of application Ser. No. 08/352,936 Dec. 9, 1994 which is a divisional of application Ser. No. 07/734,853, filed Jul. 23, 1991, now U.S. Pat. No. 5,436,305 which was a continuation-in-part of U.S. patent application Ser. No. 07/697,363 filed May 9, 1991 by three of the present co-inventors now U.S. Pat. No. 5,191,132. The disclosure of said application Ser. No. 697,363 is incorporated herein by reference.

This invention relates to organometallic compounds. More specifically, this invention relates to organometallic compounds containing at least one fluorenyl ligand. In another aspect, this invention relates to polymerization catalyst systems which contain organometallic fluorenyl compounds. In still another aspect, this invention relates to a method for polymerizing olefins using such organometallic fluorenyl compounds and to the polymers resulting from such polymerizations.

BACKGROUND OF THE INVENTION

Since the discovery of ferrocene in 1951, a number of metallocenes have been prepared by the combination of compounds having cyclopentadienyl structure with various transition metals. The term "cyclopentadienyl structure" as used herein refers to the following structure.

The term "cyclopentadiene-type compounds" as used herein refers to compounds containing the cyclopentadiene structure. Examples include unsubstituted cyclopentadiene, unsubstituted indene, unsubstituted fluorene, and substituted varieties of such compounds. Also included is tetrahydro indene.

Many of the cyclopentadiene-type metallocenes have been found useful in catalyst systems for the polymerization of olefins. It has been noted in the art that variations in the chemical structure of such cyclopentadienyl-type metallocenes can have significant effects upon the suitability of the metallocene as a polymerization catalyst. For example, the size and substitutions on cyclopentadienyl-type ligands has been found to affect the activity of the catalyst, the stereoselectivity of the catalyst, the stability of the catalyst, and other properties of the resulting polymer; however, the effects of various substituents is still largely an empirical matter, that is, experiments must be conducted in order to determine just what affect a particular variation will have upon a particular type of cyclopentadienyl-type metallocene. Some examples of some cyclopentadienyl-type metallocenes are disclosed in U.S. Pat. Nos. 4,530,914; 4,808,561; and 4,892,851, the disclosures of which are incorporated herein by reference.

While there are references in the prior art which have envisioned metallocenes containing fluorenyl groups, only a very limited number of fluorenyl-containing metallocenes have actually been prepared prior to the present invention. The Journal of Organometallic Chemistry, Vol. 113, pages 331–339 (1976), the disclosure of which is incorporated herein by reference, discloses preparing bis-fluorenyl zirconium dichloride and bis-fluorenyl zirconium dimethyl. U.S. Pat. No. 4,892,851 and the New Journal of Chemistry, Vol. 14, pages 499–503, dated 1990, the disclosures of which are incorporated herein by reference, each disclose preparing a metallocene from the ligand 1,1-dimethylmethylene-1-(fluorenyl)-1-(cyclopentadienyl). The New Journal of Chemistry article also discloses preparing a similar compound in which the cyclopentadienyl radical has a methyl substituent in the number 3 position. The term fluorenyl as used herein refers to 9-fluorenyl unless indicated otherwise.

An object of the present invention is to provide certain new fluorenyl-containing metallocenes. Another object of the present invention is to provide a method for preparing new fluorenyl-type metallocenes. Still another object of the present invention is to provide polymerization catalysts employing fluorenyl-type metallocenes. Still yet another object of the present invention is to provide processes for the polymerization of olefins using fluorenyl-type metallocene catalyst systems. Still yet another object of the present invention is to provide polymers produced using such fluorenyl-containing metallocene catalysts.

SUMMARY OF THE INVENTION

In accordance with the present invention, there are provided new metallocenes of the formula $R''_x(FlR_n)(CpR_m)MQ_k$ wherein Fl is a fluorenyl radical, Cp is a cyclopentadienyl, indenyl, tetrahydro indenyl, or fluorenyl radical, each R is the same or different and is an organo radical having 1 to 20 carbon atoms, R" is a structural bridge linking $(FlR_n)$ and $(CpR_m)$, M is metal selected from the group consisting of IVB, VB, and VIB metals of the Periodic Table, each Q is the same or different and is selected from the group consisting of hydrocarbyl or hydrocarbyloxy radicals having 1 to 20 carbon atoms and halogens, x is 1 or 0, k is an integer sufficient to fill out the remaining valences of M, n is an integer in the range of 0 to 7, m is an integer in the range of 0 to 7, further characterized by the fact that if $(CpR_m)$ is unsubstituted fluorenyl and x is 0, then n is 1 to 7, and if $(CpR_m)$ is unsubstituted cyclopentadienyl or 3-methylcyclopentadienyl and R" is 1,1-dimethyl-methylene, then n=1 to 7.

In accordance with another aspect of the present invention, there is provided a method for forming fluorenyl-containing metallocenes comprising reacting an alkali metal salt of the selected fluorenyl compound with a transition metal compound of the formula Mqk in the presence of a non-halogenated solvent for the fluorenyl salt which solvent is non-coordinating with the transition metal halide.

In accordance with still another aspect of the present invention, there is provided a process for the polymerization of olefins comprising contacting said olefins under suitable reaction conditions with a catalyst system comprising a fluorenyl-containing metallocene as described above in combination with a suitable organoaluminum co-catalyst.

Still further in accordance with the present invention there is provided the polymer products resulting from such polymerizations.

FIG. 1 is the $^{13}C$ NMR spectrum of a polymer produced by polymerizing 4-methyl-1-pentene using (1-fluorenyl-1-cyclopentadienyl methane)zirconium dichloride as a catalyst.

DETAILED DESCRIPTION OF THE INVENTION

The novel metallocenes provided in accordance with the present invention fall into two broad general categories. One category involves metallocenes in which a fluorenyl radical, either substituted or unsubstituted, is bonded to another cyclopentadienyl-type radical by a bridging structure R". These metallocenes are referred to herein as bridged metallocenes. The other category deals with metallocenes which are unbridged, that is the fluorenyl radical ligand and the other cyclopentadienyl-type ligands are bound to the metal but not to each other. These metallocenes are referred to as unbridged metallocenes. Methods for preparing fluorenyl-containing cyclopentadiene-type compounds which can be used in making the metallocenes are disclosed in the aforementioned U.S. patent application Ser. No. 697,363.

The metal, M is selected from the group IVB, VB, or VIB metals of the Periodic Table. The currently preferred metals include titanium, zirconium, hafnium, chromium, and vanadium. The R" can be selected from any suitable bridging structure. Typical examples include hydrocarbyl and heteroatom containing alkylene radicals, germanium, silicon, phosphorus, boron, aluminum, tin, oxygen, nitrogen, and the like. The R" bridge when hydrocarbyl can be aromatic in nature, such as a phenyl substituted alkylene; however, the currently preferred modes employ aliphatic alkylene bridges. The currently most preferred bridges are hydrocarbyl or heteroatom containing alkylene radical having 1 to 6 carbon atoms. In an especially preferred embodiment k is equal to the valence of M minus 2.

The substituents R can be selected from a wide range of substituents. In the preferred embodiments the substituents R are each independently selected from hydrocarbyl radicals having 1 to 20 carbon atoms. In a particularly preferred embodiment, the hydrocarbyl radicals R are alkyl radicals. More preferably the alkyl R radicals have 1 to 5 carbon atoms. Each Q is a hydrocarbyl radical such as, for example, aryl, alkyl, alkenyl, alkaryl, or arylalkyl radical having from 1 to 20 carbon atoms, hydrocarbyloxy radicals having 1 to 20 carbon atoms, or halogen.

Exemplary Q hydrocarbyl radicals include methyl, ethyl, propyl, butyl, amyl, isoamyl, hexyl, isobutyl, heptyl, octyl, nonyl, decyl, cetyl, 2-ethylhexyl, phenyl, and the like. Exemplary halogen atoms include chlorine, bromine, fluorine, and iodine and of these halogen atoms, chlorine is currently preferred. Exemplary hydrocarboxy radicals include methoxy, ethoxy, propoxy, butoxy, amyloxy, and the like.

Illustrative, but non-limiting examples of unbridged metallocenes falling within the scope of the above formula include bis(1-methyl fluorenyl) zirconium dichloride, bis(1-methyl fluorenyl) zirconium dimethyl, bis(1-methyl fluorenyl) hafnium dichloride, bis(1-t-butyl fluorenyl) zirconium dichloride, bis(2-ethyl fluorenyl) zirconium dichloride, bis(4-methyl fluorenyl)zirconium dichloride, bis(4-methyl fluorenyl)hafnium dichloride, bis(2-t-butyl fluorenyl) zirconium dichloride, bis(4-t-butyl fluorenyl) zirconium dichloride, bis(2,7-di-t-butyl fluorenyl)zirconium dichloride, bis(2,7-di-t-butyl-4-methyl fluorenyl)zirconium dichloride, and the like.

Illustrative, but non-limiting examples of metallocenes containing bridged fluorenyl ligands include for example (1,1-difluorenylmethane)zirconium dichloride, (1,2-difluorenyl)ethane zirconium dichloride, (1,3-difluorenylpropane)zirconium dichloride, (1,2-difluorenylethane)hafnium dichloride, (1,3-difluorenylpropane)hafnium dichloride, (1-fluorenyl-2-methyl-2-fluorenylethane)zirconium dichloride, dimethylsilyldifluorenyl zirconium dichloride, (1,2-di(1-methyl fluorenyl)ethane)zirconium dichloride, (1,2-di(1-methyl fluorenyl) ethane) hafnium dichloride, (1,2-di(2-ethyl fluorenyl)ethane)zirconium dichloride, (1,2-di(2-t-butyl fluorenyl)ethane)zirconium dichloride, (1,2-di(2-t-butyl fluorenyl)ethane)hafnium dichloride, (1,2-di(1-t-butyl fluorenyl)ethane) zirconium dichloride, (1,2-di(4-methyl fluorenyl) ethane) zirconium dichloride, (1,2-di(4-methyl fluorenyl)ethane) hafnium dichloride, (1,2-di(4-t-butyl fluorenyl)ethane) zirconium dichloride, 1-(fluorenyl)-1-(cyclopentadienyl)methane zirconium dichloride, 1-(fluorenyl)-1-(cyclopentadienyl)methane hafnium dichloride, 1-(2,7-di-t-butyl fluorenyl)-1-(cyclopentadienyl) methane zirconium dichloride, (1-fluorenyl-2-cyclopentadienylethane)zirconium dichloride, (1-fluorenyl-2-(3-methyl cylcopentadienyl)ethane)zirconium dichloride, (1-fluorenyl-2-indenyl ethane)zirconium dichloride, (1-fluorenyl-2-indenyl ethane)hafnium dichloride, (1-fluorenyl-2-methyl-2-indenyl ethane)zirconium dichloride, (1-fluorenyl-2-methyl-2-indenyl ethane)hafnium dichloride, (bis-fluorenylmethane)vanadium dichloride, (1,2-difluorenyl ethane)vanadium dichloride, (1-fluorenyl-1-cyclopentadienyl methane) zirconium trichloride, (1-fluorenyl-2-methyl-2-(3-methyl cyclopentadienyl) ethane)zirconium dichloride, (1-(1-methyl fluorenyl)-2-(4-methyl fluorenyl)ethane)zirconium dichloride, (1-(2,7-di-t-butyl fluorenyl)-2-(fluorenyl)ethane)zirconium dichloride, (1,2-di(2,7-di-t-butyl-4-methyl fluorenyl)ethane)zirconium dichloride, and the like.

Particularly preferred metallocene species include bridged and unbridged metallocenes containing at least one substituted fluorenyl radical, i.e., there is at least one $FlR_n$ wherein n is 1 to 7.

The inventive metallocenes as well as related metallocenes can be prepared by reacting an alkali metal salt of the bridged or unbridged fluorenyl compounds with a suitable transition metal compound in a suitable solvent under suitable reaction conditions.

The term transition metal compound as used herein includes compounds of the formula MQk wherein Me, Q, and k are as defined above. Some non-limiting examples include zirconium tetrachloride, hafnium tetrachloride, cyclopentadienyl zirconium trichloride, fluorenyl zirconium trichloride, 3-methylcyclopentadienyl zirconium trichloride, indenyl zirconium trichloride, 4-methyl fluorenyl zirconium trichloride, and the like.

The currently preferred unbridged metallocenes are prepared by reacting a substituted fluorenyl alkali metal salt with an inorganic halide of the Group IVB, V B, VIB metals to form a bis(substituted fluorenyl) metal halide. In an especially preferred embodiment bridged fluorenyl compounds of the formula (FlRn)R"(CpRm) are used wherein Fl, R, R", and m are as defined above, and where n is 1 to 7, most preferably 1 to 4.

Metallocenes in which Q is other than a halogen can be readily prepared by reacting the halide form of the metallocene with an alkali metal salt of the hydrocarbyl or hydrocarbyloxy radical under conditions as have been used in the past for forming such ligands in prior art metallocenes. See, for example, the aforemention J. Organomet. Chem. 113, 331–339 (1976). Another approach involves reacting a compound of the formula MQk wherein at least one Q is hydrocarbyl or hydrocarbyloxy with the alkali metal salt of the bridged or unbridged fluorenyl compound.

One embodiment of the present invention involves carrying out the reaction of the fluorenyl-containing salt and the transition metal compound in the presence of a liquid diluent which is non-halogenated and non-coordinating toward the transition metal compound. Examples of such suitable liquid include hydrocarbons such as toluene, pentane, or hexane as well as non-cyclic ether compounds such as diethylether. It has been found that the use of such non-halogenated non-coordinating solvents generally allows one to obtain large amounts of substantially pure metallocenes and in a more stable form; and also often allows the reaction to be conducted under higher temperature conditions, than when THF is used as the diluent. In an especially preferred embodiment the fluorenyl-containing salt used as a ligand is also prepared in a liquid diluent that is non-halogenated and non-coordinating toward the transition metal.

The formation of the alkali metal salt of the bridged or unbridged fluorenyl compound can be formed using generally any technique known in the art. For example, such can be prepared by reacting an alkali metal alkyl with the cyclopentadienyl type compounds, the bridged compounds having two cyclopentadienyl-type radicals per molecule. The molar ratio of the alkali metal alkyl to the cyclopentadienyl type radicals present can vary, generally however, the ratio would be in the range of about 0.5/1 to about 1.5/1, till more preferably about 1/1. Typically, the alkali metal of the alkali metal alkyl would be selected from sodium, potassium, and lithium, and the alkyl group would have 1 to 8 carbon atoms, more preferably 1 to 4 carbon atoms. Preferably if the fluorenyl salt is formed using tetrahydrofuran (THF) as the liquid solvent, the salt is isolated and substantially all of the THF is removed before the salt is contacted with the transition metal halide. The molar ratio of the bridged or unbridged fluorenyl compound to the transition metal compound can vary over a wide range depending upon the results desired. Typically, however, when an unbridged fluorenyl compound is used, the molar ratio of the unbridged fluorenyl compound to the transition metal compound is in the range of from about 1 to 1 to about 2 to 1 and when a bridged fluorenyl compound is used the molar ratio of the bridged fluorenyl compound to the transition metal compound is about 1 to 1.

The resulting metallocene can be recovered and purified using conventional techniques known in the art such as filtration, extraction, crystallization, and re-crystallization. It is generally desirable to recover the metallocenes in a form that is free of any substantial amount of by-product impurities. Accordingly, recrystallization and fractional crystallization to obtain relatively pure metallocens is desireable. Dichloromethane has been found to be particularly useful for such recrystallizations. As a general rule, it has been found that the metallocenes based on unbridged fluorenyl compounds are less stable than the metallocene compounds formed from bridged fluorenyl compounds. Since the stability of the various metallocenes varies, it is generally desirable to use the metallocenes soon after their preparation or at least to store the metallocene under conditions favoring their stability. For example the metallocenes can generally be stored at low temperature, i.e. below 0° C. in the absence of oxygen or water.

The resulting fluorenyl containing metallocenes can be used in combination with a suitable co-catalyst for the polymerization of olefinic monomers. In such processes the metallocene or the co-catalyst can be employed on a solid insoluble particulate support.

Examples of suitable co-catalysts include generally any of those organometallic co-catalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethyl aluminum, tri-isobutyl aluminum, diethyl aluminum chloride, diethyl aluminum hydride, and the like.

The currently most preferred co-catalyst is an aluminoxane. Such compounds include those compounds having repeating units of the formula

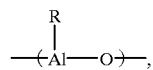

where R is an alkyl group generally having 1 to 5 carbon atoms. Aluminoxanes, also sometimes referred to as poly (hydrocarbyl aluminum oxides) are well known in the art and are generally prepared by reacting an organo hydrocarbylaluminum compound with water. Such a preparation techniques are disclosed in U.S. Pat. Nos. 3,242,099 and 4,808,561, the disclosures of which are incorporated herein by reference. The currently preferred co-catalysts are prepared either from trimethylaluminum or triethylaluminum, sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

The fluorenyl-containing metallocenes in combination with the aluminoxane co-catalyst can be used to polymerize olefins. Generally such polymerizations would be carried out in a homogeneous system in which the catalyst and co-catalyst were soluble; however, it is within the scope of the present invention to carry out the polymerizations in the presence of supported forms of the catalyst and/or co-catalyst in a slurry or gas phase polymerization. It is within the scope of the invention to use a mixture of two or more fluorenyl-containing metallocenes or a mixture of an inventive fluorenyl-containing metallocene with one or more other cyclopentadienyl-type metallocenes.

The fluorenyl-containing metallocenes when used with aluminoxane are particularly useful for the polymerization of mono-unsaturated aliphatic alpha-olefins having 2 to 10 carbon atoms. Examples of such olefins include ethylene, propylene, butene-1, pentene-1, 3-methylbutene-1, hexene-1, 4-methylpentene-1, 3-ethylbutene-1, heptene-1, octene-1, decene-1, 4,4-dimethyl-1-pentene, 4,4-diethyl-1-hexene, 3,4-dimethyl-1-hexene, and the like and mixtures thereof. The catalysts are particularly useful for preparing copolymers of ethylene or propylene and generally a minor amount, i.e. no more than about 12 mole percent, more typically less than about 10 mole percent, of the higher molecular weight olefin.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

Generally the molar ratio of the aluminum in the aluminoxane to the transition metal in the metallocene would be in the range of about 0.1:1 to about $10^5$:1 and more preferably about 5:1 to about $10^4$:1. As a general rule, the polymerizations would be carried out in the presence of liquid diluents which do not have an adverse affect upon the catalyst system. Examples of such liquid diluents include butane, isobutane, pentane, hexane, heptane, octane, cyclohexane, methylcyclohexane, toluene, xylene, and the like. The polymerization temperature can vary over a wide range, temperatures typically would be in the range of about −60° C. to about 280° C., more preferably in the range of about 20° C. to about 160° C. Typically the pressure would be in the range of from about 1 to about 500 atmospheres or greater.

The polymers produced with this invention have a wide range of uses that will be apparent to those skilled in the art from the physical properties of the respective polymer. Some of the catalysts are useful for preparing syndiotactic polymers. The term syndiotatic polymer as used herein is intended to include those polymers having segments of more than 10 monomeric repeating units in which the alkyl group of each successive monomeric unit is on the opposite side of the plane of the polymer. Generally, the polymer segments having such syndiotactic microstructure are formed of at least about 40 monomeric repeating units in which the position of the alkyl group relative to the plane of the polymer alternates from one monomeric unit to the next monomeric unit.

A further understanding of the present invention, its various aspects, objects and advantages will be provided by the following examples.

EXAMPLES

Example I

Preparation of 1-methyl fluorene

Two different reaction schemes have been used to prepare 1-methyl fluorene from fluoranthene. The reaction schemes can be illustrated by the following flow diagram. Both schemes involve the use of 1-carboxylic acid fluorenone as a starting material.

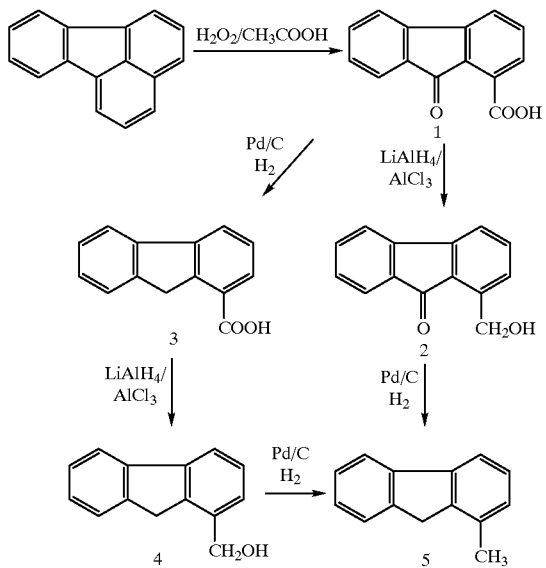

To prepare the 1-carboxylic acid fluorenone, i.e. formula 1, 20.2 g (0.1 m) of fluoranthene was dissolved in 150 ml of acetic acid at 90° C. At that temperature 200 ml of 30% aqueous $H_2O_2$, was then added gradually. Then the reaction mixture was stirred for another 3 hours at that temperature. At the beginning of the reaction, a light yellow precipitate was formed that disappeared after some time. Then the reaction mixture was cooled to 0° C. in an ice bath. An orange precipitate was formed and filtered off. The filtrate was poured into cold diluted aqueous HCl. An orange yellow precipitate was formed which was washed twice with $H_2O$ and then dissolved in an aqueous $NH_3$ solution in order to remove the unreacted fluoranthene. Then the mixture was filtered. When the filtrate was neutralized with HCl, an orange precipitate was formed. The precipitate, 1-carboxylic acid fluorenone, was filtered off and dried. The amount produced was 13.4 g.

Scheme I

About 0.76 g (0.02 mmol) of $LiAlH_4$ was suspended in a mixture of 75 ml of diethylether and 25 ml of tetrahydrofuran (dried over $LiAlH_4$). The mixture was cooled to 0° C. in an ice bath. Then 1.35 g (0.01 mmol) of $AlCl_3$ was added in small portions and the mixture was stirred at room temperature for 15 min. Then 4.2 g (0.02 mmol) of the carboxylic acid fluorenone dissolved in 400 ml of tetrahydrofuran was added via a dropping funnel while the reaction mixture was heated to reflux. Stirring was maintained for an additional 30 min. Then the reaction mixture was cooled to room temperature and the unreacted $LiAlH_4$ was destroyed with an aqueous solution of HCl. The organic phase was removed in vacuo. The solid, i.e. 1-hydroxymethyl fluorenone (formula 2), was recovered in the amount of 3.2 g. The raw 1-hydroxymethyl fluorenone can be used without further purification. 2 g of palladium on carbon catalyst containing about 10 weight percent Pd was weighed into a flask and 4.2 g (0.02 mmol) of the recovered 1-methanol fluorenone was dissolved in 250 ml tetrahydrofuran and added to the flask. The hydrogenation was conducted at room temperature with a slight overpressure of $H_2$ until 1350 ml of $H_2$ was consumed. The reaction mixture was filtered and the solvent of the filtrate was removed in vacuo. The creme colored residue was extracted with pentane, the solution was filtered over silica, and the solvent removed in vacuo. The resulting product, 1-methyl fluorene, was a colorless solid and formed in quantitative yield.

Scheme II

In the second route, the 1-carboxylic acid fluorenone is reduced using the palladium carbon catalyst in the same manner as described for converting the 1-hydroxymethyl fluorenone to 1-methyl fluorene. A quantitative yield of 1-carboxylic acid fluorene, i.e. formula 3, was obtained. The volume of hydrogen consumed was 960 ml. This product was then reduced to 1-hydroxymethyl fluorene, i.e. formula 4, by using the $LiAlH_4$ and $AlCl_3$ as described for the production of the 1-hydroxymethyl fluorenone. The 1-hydroxymethyl fluorene was then reduced using the palladium carbon catalyst and hydrogen to yield 1-methyl fluorene.

Example II

Preparation of 1-tert-butyl fluorene

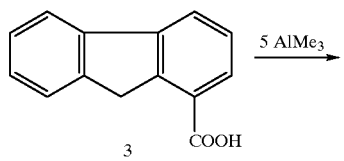

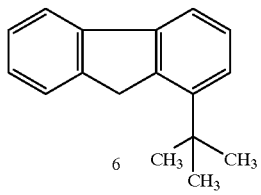

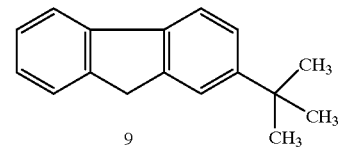

About 2 g (0.01 mmol) of 1-carboxylic acid fluorene was suspended in 50 ml of toluene. Then 4.6 ml AlMe$_3$ was added to the solution and the reaction mixture was refluxed for 10 hours. Upon heating, the reaction mixture formed a homogeneous solution. The reaction mixture was cooled to room temperature and then poured into ice cooled diluted aqueous HCl. The organic layer was separated, washed with H$_2$O, and dried over Na$_2$SO$_4$. Then the solvent was removed in vacuo. The colorless residue was extracted with pentane, the solution filtered over silica, and the solvent removed in vacuo. The yield of 1-tert-butyl fluorene, formula 6, was quantitative.

Example III

Preparation of 2-ethyl fluorene

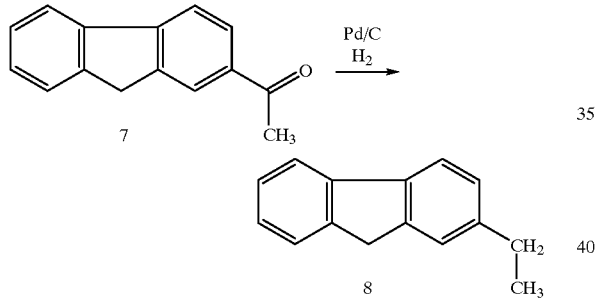

In this reaction, 2-acetyl fluorene, i.e. formula 7, was converted into 2-ethyl fluorene by hydrogenation. The hydrogenation reaction was analogous to the reaction used to convert the compound of formula 6 to the compound of formula 5. The H$_2$ volume used was 970 ml. After the removal of the solvent in vacuo, a creme colored solid was obtained. It was dissolved in pentane and the solution was filtered over silica. Pentane was removed in vacuo. The yield of 2-ethyl fluorene was quantitative.

Example IV

Preparation of 2-tert-butyl fluorene

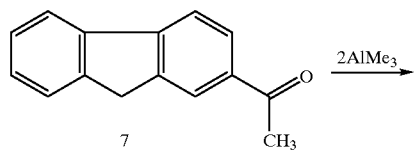

In this reaction 2-acetyl fluorene was reacted with trimethyl aluminum. The methylation was analogous to the conversion of compound 3 to compound 6 described in Example II. However, in this case, only a two-fold excess of AlMe$_3$ was necessary. The 2-tert-butyl fluorene was formed as a white solid in quantitative yield.

Example V

Preparation of 4-methyl fluorene

Two different reaction schemes have been used to prepare 4-methyl fluorene, i.e. formula 15. The schemes can be summarized as follows.

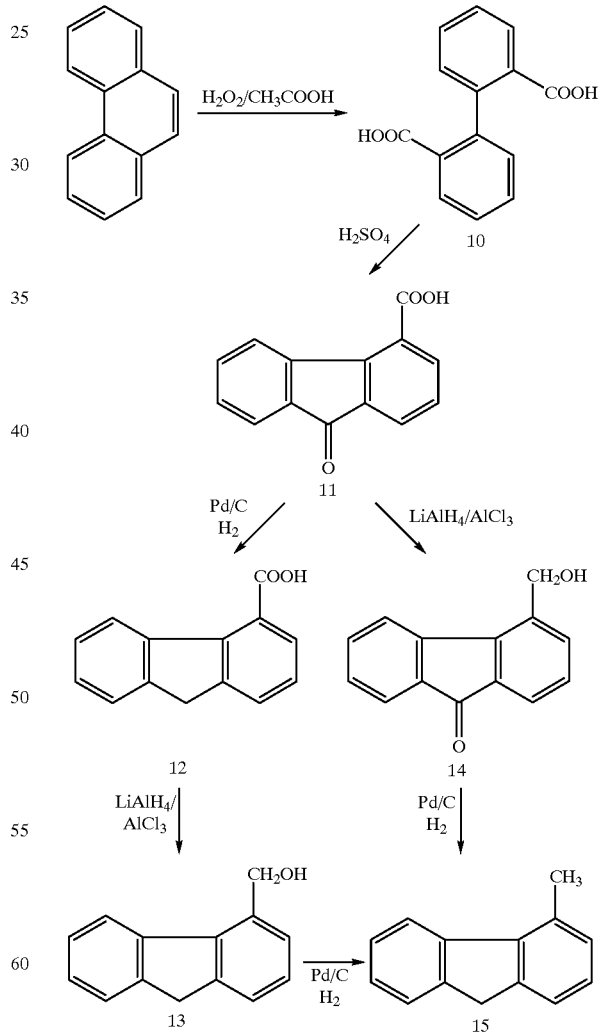

Both schemes require 4-carboxylic acid fluorenone, formula 11, as a starting material. This compound was produced from phenanthrene using a procedure similar to that disclosed in J. Org. Chem. 21, 243 (1956) except that no acetic anhydride was used. Instead, hydrogen peroxide and acetic acid were used to obtain a 67% yield of 2,2'-dicarboxylic acid biphenyl, i.e. formula 10.

The biphenyl product of formula 10 was then oxidized using sulfuric acid in the manner taught in J. Am. Chem. Soc. 64, 2845 (1942) to obtain an 82% yield of 4-carboxylic acid fluorenone, i.e. formula 11.

Scheme 1

The compound of formula 11 was reduced using LiAlH$_4$ and AlCl$_3$ in the same manner as in Example I. The reaction produced an 80% yield of 4-hydroxymethyl fluorenone, i.e. formula 14, which was then reduced using hydrogen and the palladium carbon catalyst previously described. A quantitative yield of 4-methyl fluorene resulted.

Scheme 2

The compound of formula 11 was reduced using hydrogen and the palladium carbon catalyst described previously. The reaction produced a quantitative yield of 4-carboxylic acid fluorene, i.e. formula 12. Reduction of this acid with LiAlH$_4$ and AlCl$_3$ resulted in an 80% yield of 4-hydroxymethyl fluorene, i.e. formula 13. This product was then reduced using hydrogen and the palladium carbon catalyst to produce a quantitative yield of 4-methyl fluorene.

Example VI

Preparation of 4-tert-butyl fluorene 4-carboxylic acid fluorene was reacted with trimethylaluminum generally as described in Example II to produce a 60% yield of 4-tert-butyl fluorene.

Example VII

Preparation of 2,7-bis(tert-butyl)-4-methyl fluorene

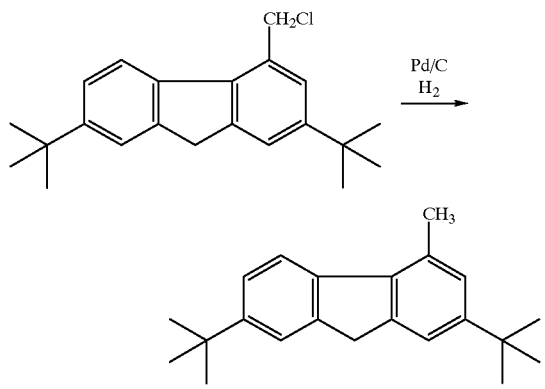

2,7-bis(tert-butyl)-4-methylene chloride fluorene was reduced using hydrogen and the palladium carbon catalyst to obtain a quantitative yield of 2,7-bis(tert-butyl)-4-methyl fluorene.

Example VIII

Preparation of 1,2-bis(9-fluorenyl)ethane

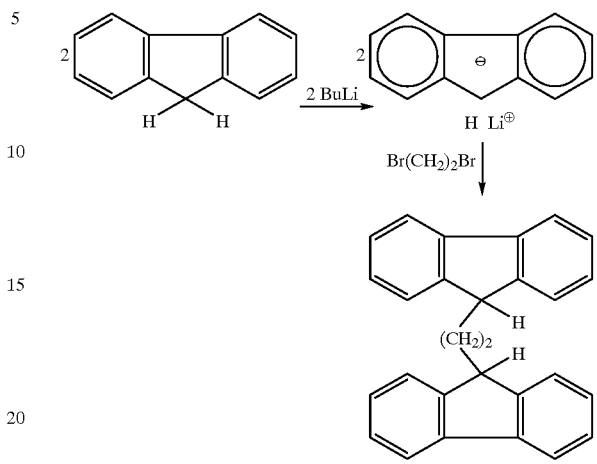

About 8.3 g (0.05 m) of fluorene was dissolved in 150 ml of tetrahydrofuran. Then 31.8 ml (0.05 m) of butyl lithium (1.6 molar in hexane) was added dropwise to this solution. After one hour, 2.3 ml (0.25 m) of dibromoethane in 25 ml of tetrahydrofuran was added. The solution was stirred for 3 hours. The yellow solution was washed with 50 ml of an aqueous NH$_4$Cl solution (5 g NH$_4$Cl/50 ml H$_2$O), then washed with 50 ml of water and then the organic phase was dried over Na$_2$SO$_4$. Then the solvent was removed in vacuo. The light yellow residue was washed twice with 25 ml of pentane. The resulting product was white. The yield was 12.5 g, i.e. a yield of about 70%, based on the moles of fluorene reacted. The product was confirmed through $^1$H NMR, $^{13}$C NMR, mass spectroscopy, and gas chromatography.

Example IX

Preparation of 1-bromo-2-(fluorenyl)ethane

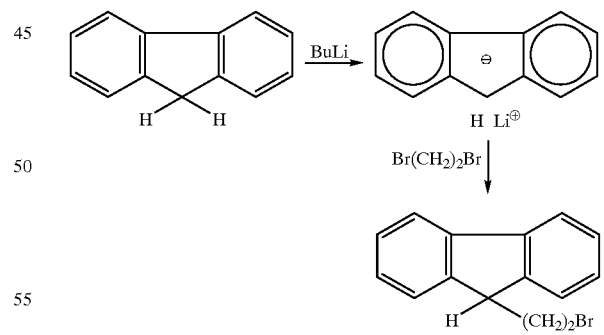

In this reaction, 8.3 g (0.05 m) of fluorene was dissolved in 150 ml of tetrahydrofuran. Then 31.8 ml (0.05 m) of butyl lithium (1.6 molar in hexane) was added dropwise to this solution. After one hour, this solution was added gradually to a stirred solution of 9 ml (0.1 m) of dibromoethane in 300 ml of pentane within 2 hours. Then the reaction mixture was treated with 50 ml of an aqueous NH$_4$Cl solution, and then washed with 50 ml of water. The organic phase was dried over Na$_2$SO$_4$. Then the solvent was removed in vacuo. The yellow residue was dissolved in pentane. The pentane solution was filtered over silica. The solution was concentrated to about 20% of the original volume and then the product was crystallized at −30° C. A yield of 10.88 g of 1-bromo-2-(fluorenyl)ethane was obtained. The product was characterized through $^1$H NMR, $^{13}$C NMR, and Mass spectroscopy.

Example X

A number of fluorenyl-containing metallocenes were prepared using either diethyl ether or toluene as a solvent.

When diethyl ether was used as a solvent, about 1 millimole of the respective bridged or unbridged fluorenyl compound was dissolved in 200 milliliters of ether. Then 1.6 molar methyllithium in diethyl ether was added to the solution to provide 1 millimole of methyllithium for each millimole of cyclopentadienyl-type radical. (An exception would be in the case in which it was desired to produce a mono-valent salt of a bridged fluorenyl compound. In such a case then only about 0.5 millimole of methyl lithium would be used for each millimole of cyclopentadienyl-type radicals.) The reaction mixture was stirred until no additional methane gas was evolved. This was done at room temperature. Next the transition metal halide was added in small portions to the solution of the fluorenyl salt. The amount of transition metal was about 0.5 millimoles when the fluorenyl compound was a monovalent salt and about 1 millimole when the fluorenyl compound was a divalent salt. The resulting solution was typically stirred for an additional 30 minutes and then concentrated to about 50 milliliters and filtered. The orange to red-colored solids remaining on the filter plate were dissolved in dichloromethane and the resulting solution was concentrated and recrystallized, generally at about −78° C.

In the runs prepared using toluene as the solvent, about 1 millimole of the bridged or unbridged fluorenyl compound was mixed in 250 milliliters of toluene. This was combined with methyllithium (1.6 molar in diethyl ether) in an amount sufficient to provide 1 millimole of methyllithium for the unbridged compounds and 2 millimoles of the methyllithium for the bridged fluorenyl compounds. (Again the exception discussed in the previous paragraph also applies.) Then the reaction mixture was heated at reflux until no more methane gas was being released. The solution was then allowed to cool to room temperature. The transition metal halide was then slowly added to the solution. Again, about 0.5 millimoles of transition metal compound was employed with the divalent fluorenyl salts and about 1 millimole was employed with the monovalent fluorenyl salts. The suspension was then stirred for about 30 minutes. The solution was then concentrated to about 50 to 75 milliliters and filtered. The orange to red solids on the filter plate were dissolved in dichloromethane and the resulting solution was concentrated and cooled to −78° C. to obtain the metallocene as a solid precipitate.

Procedures of those general types have been used to prepare the following metallocenes:

(1,2-difluorenyl ethane) zirconium dichloride; (1-fluorenyl-2-indenyl ethane) zirconium dichloride and hafnium dichloride; (1-fluorenyl-1-cyclopentadienyl methane)zirconium dichloride; (1-fluorenyl-1-cyclopentadienyl methane)zirconium trichloride, (1,2-di(2-tert butyl fluorenyl) ethane) zirconium dichloride and hafnium dichloride; (1,2-di(2-methyl fluorenyl)ethane) zirconium dichloride; (1,2-difluorenyl ethane) hafnium dichloride; bis (2,7-tert butyl-4-methyl fluorenyl)zirconium dichloride; (1,3-difluorenyl propane) zirconium dichloride and hafnium dichloride; (1-fluorenyl-2-methyl-2-fluorenyl ethane) zirconium dichloride; dimethyl silyl difluorenyl zirconium dichloride; (1,2-di(1-methyl fluorenyl)ethane) zirconium dichloride; (1,2-di(1-tert butyl fluorenyl)ethane) zirconium dichloride and hafnium dichloride; (1,2-di(2-ethyl fluorenyl)ethane zirconium dichloride and hafnium dichloride; (1,2-di(4-tert butyl fluorenyl)ethane zirconium dichloride; (1-fluorenyl-2-cyclopentadienyl ethane) zirconium dichloride; (1-fluorenyl-2-(3-methylcyclopentadienyl) ethane zirconium dichloride; (1-fluorenyl-3-indenyl propane) zirconium dichloride; (1-fluorenyl-2-methyl-2-cyclopentadienyl ethane) zirconium dichloride; (1-fluorenyl-2-methyl-2-indenyl ethane) zirconium dichloride; (1-fluorenyl-2-methyl-2-(3-methylcyclopentadienyl) ethane) zirconium dichloride; (1-(1-methyl fluorenyl)-2-(4-methyl fluorenyl)ethane) zirconium dichloride; (1-(1-tert butyl fluorenyl)-2-(4-tert butyl fluorenyl) ethane) zirconium dichloride; bis (2,7-di-tert butyl-4-methyl fluorenyl) zirconium dichloride; (1,2-difluorenyl ethane) vanadium dichloride, (1,1-difluorenyl methane) vanadium dichloride, bis(1-methyl fluorenyl) zirconium dichloride; bis (1-methyl fluorenyl) hafnium dichloride; bis(2-ethyl fluorenyl) zirconium dichloride; bis (4-methyl fluorenyl) zirconium dichloride, and bis (4-methyl fluorenyl) hafnium dichloride.

Use of Fluorenyl Metallocenes

A number of fluorenyl-containing metallocenes prepared in accordance with the present invention were evaluated for their effectiveness as catalysts for the polymerization of olefins. The specific metallocenes evaluated are referred to in the following tables as follows:

| | Catalyst |
|---|---|
| A | (1,2-difluorenyl ethane) zirconium dichloride |
| B | (1-fluorenyl-2-indenyl ethane) zirconium dichloride |
| C | (1-fluorenyl-1-cyclopentadienyl methane) zirconium dichloride |
| D | (1,2-di(2-tertbutyl fluorenyl)ethane) zirconium dichloride |
| E | bis (2,7-di-tertbutyl-4-methyl fluorenyl) zirconium dichloride |
| F | (1-fluorenyl-1-cyclopentadienyl methane) zirconium trichloride |
| G | |
| H | (1-fluorenyl-2-methyl-2-indenyl ethane) zirconium dichloride |
| I | (1,2-difluorenyl ethane) hafnium dichloride |

The polymerizations were carried out in an autoclave type reactor using methylaluminoxane as a cocatalyst. The source of the methylaluminoxane varied. In some runs a 30 weight percent toluene solution obtained from Schering was used. In other runs a 10 weight percent toluene solution of the methylaluminoxane obtained from Ethyl Corp was used. In a dry box under substantially inert conditions the solid metallocene was added to a serum vial and then a known quantity of the metallocene solution was added to the vial. The gram atom ratio of the aluminum in the aluminoxane to the metal in the metallocene was about 2200 to 1. Some of the resulting catalyst system solutions were used in more than one polymerization. Accordingly, all the catalyst system solutions were not used immediately after preparation. For optimum results it is considered desirable to use the catalyst system soon after preparation.

The catalyst system solution was added to the polymerization reactor which had been suitably prepared for the particular polymerization to be conducted. Typically for the polymerization of propylene the reactor contained liquid propylene as the reaction diluent. For polymerizations of ethylene or 4-methyl-1-pentene liquid isobutane diluent was employed. After the catalyst was charged then monomer and hydrogen, if employed, was added at room temperature. The reaction was then allowed to proceed for a period of time at which the reactor was cooled in an attempt to maintain a selected reaction temperature. In most cases after the polymerization was complete the diluent was flashed off and the polymer solids recovered and characterized. In some cases where the polymer was of low molecular weight or substantially all in solution the liquid would be drained and the unreacted monomer, comonomer, and/or diluent removed by evaporation.

Various characteristics of the polymer and the polymerization were characterized. Examples of characteristics determined in various cases include density in grams/ml (ASTM D1505-68); Melt Flow Index in grams of polymer/10 minutes (ASTM D1238-65T, Condition L); High Load Melt Index in grams of polymer/10 minutes 190° C. (ASTM D1238, Condition E); Melt Index in grams of polymer/10 minutes 190° C. (ASTM D1238, Condition E); heptane insolubles determined by the weight percent of insoluble polymer remaining after extraction with boiling heptane; melting point in degrees centigrade by Differential Scanning Calorimetry; molecular weights by size exclusion chromatography, i.e. weight average molecular weight referred to herein as Mw and number average molecular weight referred to herein as Mn; heterogenity index determined by dividing Mw by Mn. The (SEC) size exclusion chromatography was conducted using a linear column capable of resolving the wide range of molecular weights generally observed in polyolefins, such as polyethylene. The SEC used a 1,2,4-trichlorobenzene solution of the polymer at 140° C. The intrinsic viscosity was calculated from the SEC using the Mark-Houwink-Sakrada constants, i.e. $k \cdot MW^a$ in deciliters/gram, referred to in the following tables as IV. Unless indicated otherwise the conditions employed for characterizing the various properties were the same for each polymer evaluated. In some cases infrared and 13C NMR spectra were taken of the polymer. The NMR spectra were conducted on a 1,2,4-trichlorobenzene solution of the polymer. The base standard in the NMR spectra was 0 ppm based on tetramethylsilane.

Example XI

Ethylene Polymerization With (1,2 difluorenylethane) zirconium dichloride

A number of polymerization runs were conducted to evaluate the effectiveness of (1,2-difluorenylethane) zirconium dichloride as a catalyst for the polymerization of ethylene both alone and with a comonomer. The various polymerization variables and the results are summarized in the following Table. The value reported for comonomer when used in all the following tables refers to grams of the comonomer. also yield is in grams.

TABLE I

| Run | Temp. ° C. | Catalyst mg. | ΔPC2 | ΔPH2 | Hexene | Time | Yield | HLMI/MI | Density | Mw × 10³ | HI | IV |
|---|---|---|---|---|---|---|---|---|---|---|---|---|
| 1 | 90 | 0.66 | 70 | NA | NA | 20 | 29.7 | HLMI = 0 | 0.9384 | 633 | 3.9 | 5.79 |
| 2 | 70 | 0.66 | 70 | 25 | NA | 60 | 25.8 | 448/2.43 | 0.9732 | 114 | 21.8 | 1.32 |
| 3 | 70 | 1 | 70 | 25 | NA | 60 | 31.9 | 668/1.42 | 0.9759 | 116 | 19.4 | 1.34 |
| 4 | 70 | 1 | 50 | 25 | NA | 60 | 81 | 363.2/7.19 | 0.9698 | 71.9 | 10.6 | 7.1 |
| 5 | 90 | 0.66 | 70 | 2.7 | 90 | 60 | 8.15 | 5.1/.0042 | 0.8981 | 170 | 46.6 | 2.03 |
| 6 | 70 | 1.65 | 50 | NA | 90 | 70 | 161 | HLMI = 0.13 | 0.8881 | 332 | 16.8 | 3.52 |
| 7 | 70 | 3 | 135 | 10 | 50 | 45 | 130 | 288.5/0.5 | 0.9154 | 165 | 23.2 | 1.88 |
| 8 | 70 | 1 | 70 | 25 | 50 | 60 | 72.5 | 900/7.97 | 0.9297 | 159 | 27.1 | 1.8 |
| 9 | 70 | 1 | 70 | 25 | 25 | 60 | 62.1 | waxy | 0.9478 | 24.1 | 7.1 | 0.41 |
| 10 | 70 | 1 | 150 | 25 | 50 | 60 | 79 | 79.6 MI | 0.9307 | 53.5 | 8.9 | 0.79 |

The table demonstrates that the fluorenyl-containing metallocene is capable of producing polymers of ethylene having a wide range of properties. In the absence of hydrogen the polymer was a very high molecular weight material as evidenced by the low HLMI, i.e. High Load Melt Index. The data further demonstrates that copolymerization of ethylene and hexene can result in lower density polymers.

Example XII

Ethylene Polymerization with Various Bridged Fluorenyl Metallocenes

A number of ethylene polymerizations were also conducted using other bridged metallocenes. The various polymerization variables and the results are summarized in the following Table. Runs 4 and 5 from the previous Table are included for comparison.

TABLE II

| Run | Type Catalyst | Temp. | Catalyst, mg. | ΔPC2 | ΔPH2 | Hexene | Time | Yield | HLMI/MI | Density | M × 10³ | HI | IV |
|---|---|---|---|---|---|---|---|---|---|---|---|---|---|
| 4 | A | 70 | 1 | 50 | 25 | NA | 60 | 81 | 363.2/7.19 | 0.9698 | 7.9 | 10.6 | 7.1 |
| 11 | B | 70 | 1.4 | 50 | 25 | NA | 60 | 100 | 811.8/19.6 | 0.9727 | 4.7 | 6.6 | 0.78 |
| 12 | C | 70 | 1 | 70 | 25 | NA | 60 | 21 | 0.06 HLMI | 0.9517 | — | — | — |
| 13 | C | 70 | 2 | 250 | 25 | NA | 60 | 37 | 0.07 HLMI | 0.9568 | — | — | — |
| 14 | C | 70 | 2 | 70 | 3 | 90 | 60 | 137 | 18.3/0.15 | 0.8817 | 1.7 | 4.4 | 1.6 |
| 5 | A | 70 | 0.66 | 70 | 2.7 | 90 | 60 | 8.15 | 5.1/0.042 | 0.8981 | 1 | 56.6 | 2.03 |

The Table demonstrates that (1-fluorenyl-2-indenyl ethane) zirconium dichloride, i.e Catalyst B, and Catalyst C, i.e (1-fluorenyl-1-cyclopentadienyl methane) zirconium dichloride are also suitable for the polymerization of ethylene. Catalyst C gave a higher molecular weight material as indicated by the HLMI values. Run 14 demonstrates that Catalyst C is also capable of producing a copolymer of ethylene and hexene. The particular copolymer produced in this run is particularly unusual in that in contained 12.4 mole percent comonomer and a relative comonomer dispersity of 105.9. The mole percent comonomer and relative comonomer dispersity were determined from NMR spectroscopy using the technique disclosed in U.S. Pat. No. 4,522,987, the disclosure of which is incorporated herein by reference. Such a polymer can be referred to as a low density super random copolymer, i.e. a polymer having a super random distribution of the comonomer.

Example XIII

Propylene Polymerization With Various Fluorenyl Metallocenes

A number of polymerizations of propylene were conducted using various fluorenyl-containing metallocenes. The reaction variables and the results are summarized in the following Table.

Run 26 employed the bridged metallocene (1-fluorenyl-2-indenyl ethane) zirconium dichloride. Although this catalyst yielded 460 grams of solid polymer 94.4 weight percent of the polymer was a low molecular weight xylene soluble polymer. Similarly, the bridged metallocene (1-fluorenyl-2-methyl-2-indenyl ethane) zirconium dichloride in Run 27 yielded 82 grams of solid, 88 weight percent of which was low molecular weight xylene soluble material.

Runs 28 and 29 employed bridged metallocenes based on 1,2-difluorenyl ethane. Both the zirconium and the hafnium metallocenes yielded solid polypropylene.

Example XIV

Catalyst C, i.e. (1-fluorenyl-1-cyclopentadienyl methane) zirconium dichloride, was evaluated as a catalyst for the polymerization of 4-methyl-1-pentene. The amount of the metallocene employed was 5 mg. The polymerization was conducted in the presence of hydrogen with the differential pressure of the hydrogen being 25. The polymerization temperature was 120° C. and the length of the polymerization was 2 hours. The polymerization resulted in the production of 96.7 grams of a solid having a weight average molecular weight of 33,330; a heterogenity index of 1.8; and a calculated intrinsic viscosity of 0.12. About 92 weight

TABLE III

| Run | Type Catalyst | Temp. ° C. | Catalyst mg | ΔPH2 | Time | Yield | MF | Density | Mw × 10$^3$ | HI | IV | Insolubles | M.P. ° C. |
|---|---|---|---|---|---|---|---|---|---|---|---|---|---|
| 15 | C | 60 | 3 | NA | 30 | 360 | 19.6 | 0.8843 | 83.3 | 3.6 | 0.78 | 96.6 | 132.6 |
| 16 | C | 60 | 1 | NA | 60 | 230 | 14.6 | 0.8812 | 94 | 4.3 | 0.86 | 92.4 | 133.6 |
| 17 | C | 60 | 1 | 3.5 | 60 | 431 | 15.6 | 0.8829 | 89.3 | 2.3 | 0.83 | 98.1 | 134.6 |
| 18 | C | 70 | 1 | 10 | 60 | 400 | 27 | 0.8797 | 74.8 | 2.1 | 0.72 | 78.5 | 134.8 |
| 19 | C | 70 | 1 | 5 | 60 | 16 | wax | — | — | — | — | 94.7 | 133 |
| 20 | D | 60 | 2.3 | NA | 50 | 270 | — | <0.8740 | 51.6 | 2.5 | 0.55 | 93.4 | — |
| 21 | E | 60 | 1.6 | 10 | 60 | 9.5 | — | — | — | — | — | — | — |
| 22 | E | 23.4 | 1.6 | 0 | 60 | 0 | — | — | — | — | — | — | — |
| 23 | F | 70 | 2.5 | 25 | 60 | 3 | — | — | — | — | — | — | — |
| 24 | F | 70 | 2.5 | 25 | 60 | 5 | — | — | — | — | — | — | — |
| 25 | G | 70 | 12 | 10 | 60 | 41 | — | — | — | — | — | — | — |
| 26 | B | 70 | 5 | 10 | 60 | 460 | — | — | — | — | — | — | — |
| 27 | H | 70 | 2 | 10 | 60 | 82 | — | — | — | — | — | — | — |
| 28 | A | 70 | 3 | 10 | 5 | 30 | — | — | — | — | — | — | — |
| 29 | I | 70 | 5.2 | 10 | 60 | 182 | — | — | — | — | — | — | — |

Table III demonstrates that Catalyst C, i.e. (1-fluorenyl-1-cyclopentadienyl methane) zirconium dichloride, can be used to produce a polymer from propylene. The data in runs 15–17 shows that the polypropylene is highly crystalline as demonstrated by the heptane insolubles values. It is believed that the polymer contains high levels of syndiotactic molecular structure.

Run 20 demonstrates that Catalyst D, i.e. (1,2-di(2-tert butyl fluorenyl)ethane) zirconium dichloride can be used to produce a crystalline polypropylene.

Run 21 demonstrates that Catalyst E, i.e. the unbridged metallocene bis(2,7-di-tertbutyl-4-methyl fluorenyl) zirconium dichloride, produced only a small amount of solid polypropylene at 60° C. Run 22 shows that Catalyst E was not particularly effective at all at 0° C.

Run 23 and 24 employed a non-sandwich bonded metallocene, i.e. a metallocene in which only one of the cyclopentadienyl-type radicals was bonded to the transition metal. The catalyst produced only about 3 to 5 grams grams of solid polymer along with about 45 to 55 grams of low molecular weight propylene soluble polymer. Unless indicated otherwise by the formula or other means, all the bridged metallocenes referred to herein are sandwich bonded.

percent of the solid was insoluble in boiling heptane. The polymer had a melting point of 197.9° C. A 13C NMR spectrum was taken of the polymer as recovered, i.e. without heptane solubles removed, and it indicated that the polymer contained a substantial amount of syndiotactic functionality. A copy of the $^{13}$C NMR spectrum is provided in FIG. 1. Significant peaks were observed at about 22.8, 24.8, 26, 31.8, 42.8, 43.1, 46.1, and 46.2 ppm. The intensity of the peak at 43.1 ppm has greater than 0.5 of the total peak intensities in the range of 42.0 and 43.5 ppm. The peak at about 46.2 ppm had a greater intensity than any peak between the major peaks at 46.1 and 43.1 ppm. Further, the peak at about 42.8 ppm had a greater intensity than any peak between the major peaks at 46.1 and 43.1 ppm. These peak locations are relative to a peak of zero ppm for tetramethylsilane.

Example XV

Under conditions substantially as used in Example XIII, a run was carried out attempting to polymerize 4-methyl-1-pentene with Catalyst A, i.e. the bridged catalyst (1,2-difluorenyl ethane) zirconium dichloride. In this case 7 mg of the catalyst was employed and 180 grams of solid atactic wax-like polymer was obtained.

A similar run was conducted substituting the unbridged metallocene, bis(2-methylfluorenyl) zirconium dichloride for Catalyst A in the polymerization of 4-methyl-1-pentene. In this run 5 mg of the metallocene was used and 9.7 grams of solid polymer was recovered. Two samples of the polymer were subjected to heptane extraction. The extraction gave heptane insoluble values of 54.8 and 68.8. The catalyst was thus not as active as either the bridged Catalyst mentioned in the preceding paragraph or bridged Catalyst A.

That which is claimed is:

1. A metallocene of the formula (1-methylfluorenyl) (1-methylfluorenyl) $MQ_k$ where M is a metal selected from the group consisting of IVB and VB metals of the Periodic Table, each Q is the same or different and is selected from the group consisting of hydrocarbyl, hydrocarbyloxy radicals having 1 to 20 carbon atoms, and halogen, and k is 1 or 2.

2. A metallocene according to claim 1 wherein M is titanium, zirconium, or hafnium.

3. A metallocene according to claim 2 wherein each Q is a halogen, methyl, or ethyl group.

4. A metallocene according to claim 1 which is a neutral metallocene.

5. A metallocene according to claim 1 wherein M is zirconium and each Q is chlorine and k is 2.

* * * * *